United States Patent
Singh

(10) Patent No.: US 11,896,702 B2
(45) Date of Patent: Feb. 13, 2024

(54) FRAGRANCE-ENHANCING COMPOSITIONS

(71) Applicant: ALMENDRA PTE. LTD., Singapore (SG)

(72) Inventor: Inder Singh, Bangkok (TH)

(73) Assignee: Almendra PTE LTD., Singapore (SG)

( * ) Notice: Subject to any disclaimer, the term of this patent is extended or adjusted under 35 U.S.C. 154(b) by 209 days.

(21) Appl. No.: 16/905,988

(22) Filed: Jun. 19, 2020

(65) Prior Publication Data

US 2020/0397685 A1 Dec. 24, 2020

Related U.S. Application Data

(60) Provisional application No. 62/863,901, filed on Jun. 20, 2019.

(51) Int. Cl.

| | |
|---|---|
| A61K 8/60 | (2006.01) |
| A61Q 13/00 | (2006.01) |
| C11D 3/50 | (2006.01) |
| A61K 8/9789 | (2017.01) |
| A61Q 19/00 | (2006.01) |
| A61Q 19/10 | (2006.01) |
| C11B 9/00 | (2006.01) |

(52) U.S. Cl.
CPC ............ *A61K 8/602* (2013.01); *A61K 8/9789* (2017.08); *A61Q 13/00* (2013.01); *A61Q 19/002* (2013.01); *A61Q 19/007* (2013.01); *A61Q 19/10* (2013.01); *C11B 9/0015* (2013.01); *C11D 3/502* (2013.01)

(58) Field of Classification Search
None
See application file for complete search history.

(56) References Cited

U.S. PATENT DOCUMENTS

| | | |
|---|---|---|
| 2,091,162 A | 8/1937 | Schrauth |
| 3,317,397 A | 5/1967 | Saunders |
| 3,963,648 A | 6/1976 | Jones et al. |
| 4,264,478 A | 4/1981 | Seldner |
| 4,324,703 A | 4/1982 | Seldner |
| 4,612,942 A | 9/1986 | Dobberstein et al. |
| 6,172,037 B1 | 1/2001 | Perring et al. |
| 8,524,785 B2 | 9/2013 | Dewis et al. |
| 9,420,815 B2 | 8/2016 | Purkayastha et al. |
| 9,750,673 B2 | 9/2017 | Chevet et al. |
| 2012/0329738 A1 | 12/2012 | Liu |
| 2016/0128371 A1 | 5/2016 | Purkayastha et al. |
| 2016/0295892 A1 | 10/2016 | Schafer et al. |
| 2017/0137744 A1 | 5/2017 | Limketkai et al. |
| 2017/0332673 A1* | 11/2017 | Philippe .................. A23L 27/36 |
| 2018/0037844 A1* | 2/2018 | Foley ....................... C11D 3/50 |

FOREIGN PATENT DOCUMENTS

| | | |
|---|---|---|
| CN | 105451710 A | 3/2016 |
| CN | 105636453 A | 6/2016 |
| CN | 107995845 A | 5/2018 |
| CN | 109805440 A | 5/2019 |
| JP | H05276872 A | 10/1993 |
| RU | 2464815 C1 | 10/2012 |
| WO | 2006087370 A1 | 8/2006 |
| WO | 2012128775 A1 | 9/2012 |
| WO | 20120128775 | 9/2012 |

OTHER PUBLICATIONS

Zhang, Meiying, Tongcheng Dai, and Nianping Feng, "A Novel Solubility-Enhanced Rubusoside-Based Micelles for Increased Cancer Therapy," Nanoscale Research Letters, 2017, pp. 1-10, vol. 12, No. 274, doi: 10.1186/s11671-017-2054-4.
Office Action for CN Application No. 202080044847.3 dated Jul. 19, 2023. (partial translation).
Office Action for Indonesian Application No. P00202200460 dated Aug. 14, 2023.
Chinese Office Action, China Patent Application No. 202080044847.3, dated Jul. 14, 2023.

* cited by examiner

*Primary Examiner* — David J Blanchard
*Assistant Examiner* — Sarah J Chickos
(74) *Attorney, Agent, or Firm* — Perilla Knox & Hildebrandt LLP; Stephanie L. Davy-Jow

(57) ABSTRACT

Long-lasting fragrance compositions are provided for. The fragrance compositions can include at least one fragrance compound and a glycoside. The glycoside can be selected from a Steviol glycoside, a glucosylated Steviol glycoside, a derivative of a Steviol glycoside, a derivative of a glucosylated Steviol glycoside, or combinations thereof. Also provided for are products including a long-lasting fragrance composition as above. The products can include perfumes, body care products, cosmetics, cleaning and laundry products, and the like.

20 Claims, No Drawings

FRAGRANCE-ENHANCING COMPOSITIONS

CROSS-REFERENCE TO RELATED APPLICATIONS

This application claims the benefit of and priority to U.S. Provisional Application Ser. No. 62/863,901, having the title "FRAGRANCE-ENHANCING COMPOSITIONS", filed on Jun. 20, 2019, the disclosure of which is incorporated herein by reference in its entirety.

BACKGROUND

A fragrance is a mixture of individual components both aromatic and non-aromatic. Each fragrance component interacts both with other components within the mixture, and with the chemical and structural nature of the environment to determine the aesthetic and the physical characters of the final system. The combined talents of the perfumer and the technical staff, working closely together, are needed to create a fragrance mixture that will provide a top note, a middle note and a base note. The top note is characterized by the upfront refreshing quality when the fragrance is applied, while the base note is the scent that continues to linger and stays for a long time with the wearer. The middle note is what bridges both the top note and the base note, providing a pleasant transition from the top note to the base note.

One of the components used in the fragrance mixture is called a fixative and is generally used to prolong the fragrance effect of the fragrance mixture by delaying the evaporation rate of volatile materials in the fragrance mixture. This is achieved through hydrogen bonding of the fixative component with the other components resulting in an overall lower vapor pressure for the fragrance mixture. A good fixative generally will not be odorous by itself, will be miscible in polar and nonpolar solvents, and will have a higher boiling point than the other components in the fragrance mixture. Typical examples of fixatives are floral and botanical absolutes, concretes and oleo resin, animal secretions and extracts, macrocyclic musks, and nitro musks.

It is well known that fragrance fixatives (also referred to as fragrance carriers) are generally synthetically produced chemicals and those that are natural can distort the nature or character of the fragrance being fixed.

Despite advances in fragrance research, there is still a scarcity of compounds that are both potent and efficacious fragrance fixatives without interfering with the intended scent. These needs and other needs are satisfied by the present disclosure.

SUMMARY

Embodiments of the present disclosure provide for compositions including glycosides, products including glycosides, and the like.

An embodiment of the present disclosure includes fragrance compositions including at least one fragrance compound and a glycoside. The glycoside can be selected from a Steviol glycoside, a glucosylated Steviol glycoside, a derivative of a Steviol glycoside, a derivative of a glucosylated Steviol glycoside, or combinations thereof.

An embodiment of the present disclosure also includes products including a fragrance composition as above. The products can include such as a perfume, an eau de toilette, a lotion, a soap, a cosmetic, a body care product, a dishwashing detergent, a surface cleaner, an air freshener, a softener, a bleach, or a laundry detergent.

An embodiment of the present disclosure also includes non-comestible product comprising a perfume, the perfume comprising water, a solvent, a glycoside, and a fragrance compound Other compositions, apparatus, methods, features, and advantages will be or become apparent to one with skill in the art upon examination of the following drawings and detailed description. It is intended that all such additional compositions, apparatus, methods, features and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry and the like, which are within the skill of the art.

The following examples are put forth so as to provide those of ordinary skill in the art with a complete disclosure and description of how to perform the methods and use the compositions and methods disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

Definitions

A "fragrance compound" as used herein, also known as an odorant, aroma, or fragrance, is a chemical compound that has a smell or odor, and is sufficiently volatile to be transported to the olfactory system in the upper part of the nose. "Aromatic," as used herein, refers to a characteristic of being an odorant. Aromatics can be derived from plant sources (such as bark, fruit, flowers, resins, etc.), animal sources (such as honey, musks, castoreum, etc.), other natural sources (such as lichen, seaweed, etc.), or synthetic sources.

Rebaudioside A 80% has Rebaudioside A as the principal component at minimum 80% and the other glycosides at 20% on a dry basis. Similarly, Rebaudioside A 97%, has Rebaudisoide A as the principal component at a minimum of 97% with the balance being other glycosides on a dry basis.

"Glycosylation" as used herein describes the number of glucose molecules attached to the steviol glycosides. A low degree of glycosylation can include from one to five glucose molecules. A high degree of glycosylation can include from five to twenty glucose molecules.

"Alcohols," as used herein, can include but are not limited to terpene alcohols (e.g. linalool, citronellol, geraniol, nerol, terpineol, α-terpineol, dihydromyrcenol, farnesol, nerolidol, cedrol, menthol, and borneol), aromatic alcohols (e.g. phenylethyl alcohol, benzyl alcohol, dimethyl benzyl carbinol, phenylethyl dimethyl carbinol, and phenyl hexanol), and aliphatic alcohols (e.g. cis-3-hexenol, 1-(2,2,6-trimethylcyclohexyl)-3-hexanol, Amber Core (Trade Name of Kao Corporation, 1-(2-tert-butyl cyclohexyloxy)-2-butanol), Sandalmysore Core (Trade Name of Kao Corporation, 2-methyl-4-(2,2,3-trimethyl-3-cyclopenten-1-yl)-2-buten-1-ol), Magnol (Trade Name of Kao Corporation, a mixture containing, as a main component, 3(4)-(5-ethylbicyclo[2.2.1]heptyl-2)-cyclohexanol), Undecavertol (Trade Name of Givaudan Roure K.K., 4-methyl-3-decene-5-ol), and isobornylcyclohexanol).

As used herein, the phrase "natural high-potency sweetener" (or "NHP sweetener" or "NHPS") means any sweetener found in nature which may be in raw, extracted, purified, or any other form, singularly or in combination thereof and characteristically have a sweetness potency greater than sucrose, fructose, or glucose, yet have less calories. Non-limiting examples of NHPSs include: rebaudioside A, rebaudioside B, rebaudioside C, rebaudioside D, rebaudioside E, rebaudioside F, dulcoside A, dulcoside B, rubusoside, *stevia*, stevioside, other steviol glycoside extract components, mogroside II, mogroside III, mogroside IV, mogroside V, mogroside VI, isomogroside V, 11-oxomogroside, siamenoside, Luo Han Guo sweetener, other Luo Han Guo extract components, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, cyclocarioside I, and modification or derivatives thereof. NHPS also includes modified NHPSs. Modified NHPSs can include NHPSs which have been altered naturally or synthetically. For example, a modified NHPS includes NHPSs that have been fermented, contacted with enzyme, or derivatized or substituted on the NHPS. For the sake of brevity, in the description of embodiments, a modified NHPS is not expressly described as an alternative to an unmodified NHPSs, but it should be understood that modified NHPSs can be substituted for NHPSs in any embodiment disclosed herein.

"Perfume" as used herein describes a product generally used as a topically applied fragrance, which may be applied as a spray or directly to the skin. Perfume can also include cologne, eau de toilette, eau de partum, after shave, or similar products as would be understood by one of ordinary skill in the art. In an aspect, the perfume does not include comestible products containing fragrance. In another aspect, the perfume is non-comestible. In yet another embodiment, the perfume is not intended to be comestible.

"Comestible", as used herein, refers to products that are fit to be eaten and/or generally intended to be ingested (e.g. food or beverages). Similarly, "non-comestible" refers to products not intended for oral consumption (e.g. body products, household cleaning products, fine fragrance products). Such non-comestible products may be non-toxic if ingested but are not typically understood to be foods or beverages.

General Discussion

In accordance with the purpose(s) of the present disclosure, as embodied and broadly described herein, embodiments of the present disclosure, in some aspects, relate to fragrance compositions and products including fragrance compositions.

In general, embodiments of the present disclosure provide fragrance compositions including at least one fragrance compound as well as a glycoside. According to the disclosed embodiments, the glycoside can comprise one or more steviol-based glycosides including Steviol glycosides, glucosylated Steviol glycosides, derivatives of a Steviol glycoside, derivatives of a glucosylated Steviol glycoside, or combinations thereof.

Advantageously, the addition of a glycoside provides enhanced duration of a fragrance. Steviol-based glycosides have been extensively tested and are known to be safe for humans.

The use of Steviol glycosides, glucosylated steviol glycosides and its derivatives as a fixative in a fragranced products increases the lasting power of the fragrance dramatically. The increase of the lasting power does not distort the character of the fragrance. In other words, the perceived fragrance of a fragrance composition comprising the glycoside is substantially the same as the perceived fragrance of a similar fragrance composition that lacks the glycoside component. These properties are a unique and unexpected character of a steviol-based glycoside.

According to various embodiments of the present disclosure the fragrance composition comprises about 0.001 to about 5 weight %, or about 0.01 to about 3%, or about 0.10 to about 1%, of the glycoside, based on the total weight of the fragrance composition. Advantageously, the inclusion of a steviol-based glycoside in a fragrance composition can prolong the time for which a fragrance is perceivable, from about 8 hours to 48 hours longer than compositions without the steviol-based glycoside. In some embodiments, the fragrance composition including the glycoside can enable a reduction in the amount of fragrance compound (e.g. from about 10% up to 30% less) needed in a composition to provide the same perceived fragrance. Such benefits can reduce the cost of manufacturing products that include fragrance, such as perfumes, cosmetics, and household products. Advantageously, the inclusion of the steviol-based glycoside can simultaneously reduce the amount of fragrance compound needed to detect a fragrance and increase the duration for which the fragrance can be detected.

In various embodiments, the glycoside can include diterpines (e.g. rubusoside, Rebaudioside A, Rebaudioside B, Rebaudioside C, Rebaudioside D, Rebaudioside E, Rebaudioside F, Rebaudioside M, Rebaudioside N, Rebaudioside O, dulcoside A, or enzymatically treated stevia extract). The inclusion of a Steviol-based glycoside does not interfere with the perceived fragrance of a composition. It is envisioned that other natural high-potency sweeteners and/or their derivatives could be used, including but not limited to, triterpines (e.g. monkfruit) and glycyrrhizin (e.g. licorice root extract).

The glucosylated Steviol glycoside can have a low degree of glycosylation, where number of glucose molecules attached to the steviol glycosides is from one to five. Alternatively, the glucosylated Steviol glycoside can have a high degree of glycosylation, where number of glucose molecules attached to the steviol glycosides is from six to twenty.

The Steviol glycosides, glucosylated steviol glycosides and their derivatives of the present disclosure can be extracted from the plant *Stevia rebaudiana bertoni*. The process of extraction is well established. According to one process, the leaves of the plant are soaked in water for a number of hours, resulting in an aqueous solution that is rich in glycosides. Next, the aqueous solution can be processed in a series of steps of filtration to remove unwanted components. Finally, the aqueous solution is spray dried, resulting in a white-yellowish powder. For glucosylated steviol glycosides, this white-yellowish powder is further dissolved in water and processed with enzymes after adjusting the pH and temperature together with a carbohydrate source (e.g. starch or dextrins). The derivatives are generally produced by reacting chemicals with *Stevia* extract. There are no known examples of using Steviol glycosides, glucosylated steviol glycosides, or their derivatives as a fixative in fragranced product.

The addition of an effective amount of steviol-based glycosides to fragrance mixtures resulted in fragrance fixing, without detectably altering the fragrance of the mixtures. Neither Steviol glycosides, glucosylated steviol glycosides, nor their derivatives have a detectable fragrance, so their use as fragrance-enhancing or fragrance fixing components in topical or non-food applications has not heretofore been appreciated.

Although not intending to be bound by theory, it is hypothesized that the steviol-based glycosides are nanoencapsulating the less-soluble fragrance compounds in the mixture, allowing them to more slowly evaporate, thereby elongating the fragrance availability.

Interesting effects of steviol glycosides have been shown in other fields such as pharmaceuticals, including increasing absorption of insoluble or poorly soluble bioactive materials. Low water solubility of bioactive compounds, resulting in their use at very high concentrations to deliver a desired pharmacological effect, is problematic and results in negative side effects of the medicines among subjects. Surfactants can be used, in part, to increase solubility/bioavailability of bioactive compounds to the target cells and reduce the over stimulation of non-target cells incidentally exposed during a medical treatment. Sonication at high temperature and homogenization at high temperature and pressure of aqueous solutions of steviol glycoside "surfactant" and bioactive compounds are two techniques shown to further stabilize the systems to the extent that they are resistant to changes in pH, temperature and remain intact after drying and reconstitution.

In accordance with various embodiments of the present disclosure, fragrance compounds can be any ingredient or combination of ingredients providing an odor to the fragrance composition or to an object or product to which it is provided. The fragrance compounds can be natural, synthetic, or a combination thereof. Fragrance compounds can include ethereal oils and extracts (e.g. castoreum, costus root oil, oak moss absolute, geranium oil, jasmine absolute, patchouli oil, rose oil, sandalwood oil, ylang-ylang oil), alcohols (e.g. citronellol, Ebanol™, eugenol, geraniol, Super Muguet™, linalool, phenylethyl alcohol, Sandalore™, terpineol or Timberol™), aldehydes and ketones (e.g. Azurone™, α-amylcinnamaldehyde, Georgywood™, hydroxycitronellal, Iso E Super™, Isoraldeine™, Hedione™, maltol, methyl cedryl ketone, methyl ionone or vanillin), ether and acetals (e.g. Ambrox™, geranyl methyl ether, rose oxide or Spirambrene™), esters and lactones (e.g. benzyl acetate, cedryl acetate, γ-decalactone, Helvetolide™, Serenolide™, γ-undecalactone or vetivenyl acetate), macrocycles (e.g. ambrettolide, ethylene brassylate or Exaltolide™), and heterocycles (e.g. isobutylchinoline).

Other fragrance compounds, also referred to as perfume raw materials can include, but are not limited to, ethyl 2,4 decadienoate, allyl heptoate, amyl acetate, ethyl butyrate, Grapefruit Zest (C&A), prenyl acetate, pinoacetaldehyde, 2,6-nonadienol, 3,6-nonadienol, cis-6-nonenol, excital, ebanol, polysantol, orange juice carbonyls, lemon juice carbonyls, orange sinensal, paradiff, tangerinal, benzaldehyde, mandarin aldehyde, undecalactone, norlimbanol, decyl aldehyde, trans-2-hexenal, trans-2-decenal, damascenone, 2-isobutylthiazole, 4-methyl-4-mercaptopentan-2-one, corps cassis 0.1% TEC, patchouli, 2-methoxy-4-vinylphenol, pyridine acetyl 10%, sulfurol, diacetyl, furaneol, maple lactone, allyl amyl glycolate, Ambroxan, alpha damascone damascene, Cetalox, cyclal C, Cedramber, cyclo galbanate, Galbex, Cymal, nerol, Florhydral, P.t. bucinal, iso cyclo citral, Fructone, methyl iso butenyl tetrahydro pyran, Frutene, Delphone, ethyl methyl phenyl glycidate, Violiff, for acetate, Delta damascone damascene, Ambrox, Calone, iso eugenol, Hivemal, methyl beta napthyl ketone, Ozonil, benzyl salicylate, Spirogalbone, cinnamic alcohol, Javanol, dihydro iso jasmonate, Adoxal, Kharismal, pyrazines, ethyl anthranilate, aldehyde supra, Bacdanol, Anethol, irisantheme, yara yara, Keone, cis 3 hexenyl salicylate, methyl nonyl ketone, coumarin, gamma dodecalactone, Applinate, eucalyptol, intreleven aldehyde, heliotropin, indol, Manzanate, ionone, alpha, trans 4 decenal, ionone beta, Oxane, neobutanone, Clonal, methyl octine carbonate, Floralozone, methyl heptine carbonate, methyl nonyl acetaldehyde, Cashmeran, phenoxy ethyl iso butyrate, phenyl acetaldehyde, ethyl methyl phenyl glycidate, undecyl aldehyde, Aurantiol, nectaryl, buccoxime, Laurie aldehyde, nirvanol, Trifemal, pyrazobutyle, Veloutone, Anisic aldehyde, paramenthene, isovaleric aldehyde 0.1% DPG, liminal, labienoxime, rhubofix, iso propyl quinoline, 4-(2,6,6-Trimethyl-1-cyclohexenyl)-3-butenone-2; (3aR-(3aalpha,5abeta,9aalpha,9bbeta))-dodecahydro-3a,6,6,9a-tetramethyl naphtha(2,1-b)furan; 2,6-Dimethyl-5-heptenal; 3,7-Dimethyl-1,6-octadien-3-ol; 3-Methyl-2-buten-1-yl acetate; 3,7-Dimethyl-2,6-octadienenitrile; 2,4-Dimethylcyclohexene-3-carbaldehyde; Phenyl Acetaldehyde, Indol, ethyl methyl dioxolane acetate; 4-(2,6,6-Trimethyl-1,3-cyclohexadienyl)-3-buten-4-one;

Cis 3 Hexenyl Acetate; Lauric Ald, Tricyclo decenyl acetate, Para cresyl methyl ether, 7-acetyl, 1,2,3,4,5,6,7,8-octahydro-1,1,6,7-tetramethyl naphthalene; 3-buten-2-one; 3-methyl-4-(2,6,6-trimethyl-2-cyclohexen-1-yl); Acetic acid (Cyclohexyloxy), 2-propenyl ester; 3-buten-2-one, 4-(2,6,6-trimethyl-2-cyclohexen-1-yl), (E); Decyl Aldehyde, Methyl-3,4-dioxy(cylcoacetonyl) benzene; 2,6-Dimethyl-2,6-octadien-8-ol; ortho tertiary butyl cyclohexanyl acetate; Hexanoic acid,2-propenyl ester; 4-Methoxybenzaldehyde; 3-(3-Isopropylphenyl)butanal; Iso 2-Methoxy-4-(2-propenyl) phenol, Tetra Hydro 3,7-Dimethyl-1,6-octadien-3-ol; 1-methyl-4-isopropenyl-1-cyclohexene; Methyl phenyl carbonyl acetate; galaxolide; Hexahydro-4,7methano-1H-inden-5 (or 6)-yl propionate; Benzaldehyde, 3,7-Dimethyl-2,6-octadienal; 3,3-Dimethyl-5-(2,2,3-trimethyl-3-cycloenten-1-yl)-4-penten-2-ol; 2-Methoxy-4-(2-propenyl) phenol; 3,7-Dimethyl-6-octen-1-ol; Allyl heptanoate; 1,3-Oxathiane, 2-methyl-4-propyl-, cis-; paradiff; (all-E)-alpha-sinensal, 2,6,10-trimethyl-2(E),6(E),9(E),11-dodecatetraenal; mandarin aldehyde, p-l-menthen-8 thiol; 4-Methyl-3-decen-5-ol; Ethyl caproate, Ethyl-2-4-decadienoate, 4-Penten-1-one, 1-(5,5-Dimethyl-1-cyclohexen-1-yl)-; 1H-Indene-a-propanal, 2,3-dihydro-1,1-dimethyl-(9Cl); Methyl nonyl acetaldehyde; Orange juice Carbonyls; 4 dodecenal; 3-cyclohexene-1-carboxaldehyde, 2,4-dimethyl; 2,6,-nonenol; 2,6-nonadeinal; 2,6-nonadienol; 3-P-cumenyl-propionaldehyde 4-(1-methylethyl)-benzenepropanal; 1-(2,6,6-Trimethyl-1,3-cyclohexandienyl)-2-buten-1-one; 6-(Z,3-pentenyl)-tetrahydro-(2H)-pyranone-2; 3-Methyl-(cis-2-penten-1-yl)-2-cyclopenten-1-one. 2,6 nonenol; 2,6-nonadienol; (3aR-(3 aalpha,5abeta,9aalpha,9bbeta))-dodecahydro-3a,6,6,9a-tetramethyl naphtha(2,1-b)furan; Beta Gamma Hexenol; Cis 3 Hexenyl Acetate; 3-P-cumenyl-propionaldehyde 4-(1-methylethyl)-benzenepropanal; 1-(2,6,6-Trimethyl-1,3-cyclohexandienyl)-2-buten-1-one; 3-(3-lsopropylphenyl) butanal; 4-Penten-1-one, 1-(5,5-Dimethyl-1-cyclohexen-1-yl)-; 1H-Indene-a-propanal, 2,3-dihydro-1,1-dimethyl-(9Cl); 4-(2,6,6-Trimethyl-1-cyclohexenyl)-3-butenone-2; 6-(Z,3-pentenyl)-tetrahydro-(2H)-pyranone-2; 2,6-Dimethyl-5-heptenal; 6,6-Dimethylbicyclo{3.1.1)Hept-2-ene-2-proponal; 3-cyclohexene-1-carboxaldehyde, 2,4-dimethyl; 4-Methyl-3-decen-5-ol; ortho tertiary butyl cyclohexanyl acetate; 3-Methyl-(cis-2-penten-1-yl)-2-cyclopenten-1-one; 4-Pentene-2-ol, 3,3-dimethyl-5-(2,2,3-trimethyl-3-cyclopenten-1-yl)-. Benzaldehyde; Undeclactone; 4-(2,6,6-Trimethyl-1-cyclohexenyl)-3-butenone-2; Allyl Heptanoate; 1,3-Oxathiane, 2-methyl-4-propyl-, cis-; Paradiff, (all-E)-alpha-sinensal, 2,6,10-trimethyl-2(E),6(E),9(E),11-dodecatetraenal; mandarin aldehyde; 4-dodecenal; p-1-menthen-8 thiol; Orange Juice Carbonyls; Decyl Aldehyde; 4-Methyl-3-decen-5-ol; 4-Penten-1-one, 1-(5,5-Dimethyl-1-cyclohexen-1-yl)-. Hexanoic acid,2-propenyl ester; 4-Methoxybenzaldehyde; Allyl Heptanoate; Benzaldehyde; 1,3-Oxathiane, 2-methyl-4-propyl-, cis-; Decyl Aldehyde; Ethyl 2'4-decadienoate; Ethyl Caproate; 4-Penten-1-one, Dimethyl-1-cyclohexen-1-yl)-; p-1-menthen-8 thiol; (all-E)-alpha-sinensal 2,6,10-trimethyl-2(E),6(E),9(E),11-dodecatetraenal; 1H-Indene-a-propanal, 2,3-dihydro-1,1-dimethyl-(9C1); 4-(2,6,6-Trimethyl-1-cyclohexenyl)-3-butenone-2; 3 dodecenal; Methyl Nonyl Acetaldehyde; Orange Juice Carbonyls; Paradiff; 4 dodecenal; 3-cyclohexene-1-carboxaldehyde, 2,4-dimethyl; 4-Methyl-3-decen-5-ol; animal fragrances such as musk oil, civet, castoreum, ambergris; plant fragrances such as nutmeg extract, cardomon extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomille oil, clove oil, sage oil, neroli oil, labdanum oil, *eucalyptus* oil, *verbena* oil, *mimosa* extract, *narcissus* extract, carrot seed extract, jasmine extract, olibanum extract, rose extract, acetophenone, adoxal, aldehyde C-12, aldehyde C-14, aldehyde C-18, allyl caprylate, allyl heptanoate, ambroxan, dimethylindane derivatives, anethole, anisaldehyde, benzaldehyde, benzyl acetate, benzyl alcohol and ester derivatives, benzyl propionate, benzyl salicylate, beta gamma hexanol, borneol, butyl acetate, camphor, carbitol, carvone, cetalox, cinnamaldehyde, cinnamyl acetate, cinnamyl alcohol, cis-3-hexanol and ester derivatives, cis-3-hexenyl methyl carbonate, cis jasmone, citral, citronnellol and ester derivatives, cumin aldehyde, cyclamen aldehyde, cyclo galbanate, damascones, decanol, decyl aldehyde, estragole, delta muscenone, dihydromyrcenol, dimethyl benzyl carbinol, 6,8-dimethyl-2-nonanol, dimethyl benzyl carbinyl butyrate, ethyl isobutyrate, ethyl propionate, ethyl caprylate, ethyl cinnamate, ethyl hexanoate, ethyl valerate, exaltolide, fenchone, galaxolide, geraniol and ester derivatives, hedione, helional, 2-heptonone, hexenol, hexyl salicylate, hydroxycitrolnellal, ionones, isoeugenol, isoamyl iso-valerate, iso E super, linalool acteate, lilial, lyral, majantol, mayol, menthol, p-methylacetophenone, methyl cedrylone, methyl dihydrojasmonate, methyl eugenol, mugetanol, para hydroxy phenyl butanone, phenoxynol, phenyl-acetaldehyde dimethyl acetate, phenoxyethyl isobutyrate, phenyl ethyl alcohol, pinenes, sandalore, sanjinol, santalol, thymol, terpenes, tonalide, 3,3,5-trimethylcyclohexanol, undecylenic aldehyde, phenyl ethyl alcohol, linalool, geraniol, citronellol, cinnamic alcohol, iso bornyl acetate, benzyl acetate, para-tertiary-butyl cyclohexyl acetate, linalyl acetate, dihydro-nor-dicyclopentadienyl acetate, dihydro-nor-dicyclopentadienyl propionate, amyl salicylate, benzyl salicylate, para-iso-propyl alpha-octyl hydrocinnamic aldehyde, hexyl cinnamic aldehyde, hydroxy citronellal, heliotropin, anisaldehyde, citral, dextro limonene, coumarin, ionone gamma methyl, methyl beta naphthyl ketone, gamma undecalactone, eugenol, musk xylol, 1,3,4,6,7,8-hexahydro-4,6,6,7,8,8-hexamethylcyclopenta-gamma-2-benzopyrane, 4-acetyl-6-tertiarybutyl-1,1-dimethyl indan, 6-acetyl-1,1,3,4,4,6-hexamethyl tetrahydro naphthalene, beta naphthyl ethyl ether, methyl eugenol, methyl cedrenyl ketone, patchouli, lavandin, geranyl nitrile, alpha ionone, alpha beta ionone, benzyl iso eugenol, amyl cinnamic aldehyde, beta gamma hexenol, orange CP, orthotertiary-butyl cyclohexyl acetate, 2-methyl-3-(para-iso-propylphenyl)propionaldehyde, trichloro methyl phenyl carbinyl acetate, nonane diol-1,3-acetate, methyl dihydro jasmonate, phenoxy ethyl iso butyrate, citronella, citronellal, citrathal, tetrahydromuguol, ethylene brassylate, musk ketone, musk tibetine, phenyl ethyl acetate, oakmoss 25%, hexyl salicylate, eucalyptol, Stemone, Cashmeran, GERANIOL, Citronellyl nitrile, Linalool, Ethyl linalool, Benzyl acetate, Undecavertol, Methyl Phenyl Carbinyl Acetate, 6-Nonen-1-ol, (6Z)-, Benzyl propionate, Iso-E Super, 2,6-Nonadien-1-ol, (2E,6Z)-(10% Nonadienol in DPG), cis-3-Hexen-1-ol (beta gamma hexenol), Isobornyl acetate, Ambrox DL, ozone propanal (Floralozone), 3-methyl-5-(2,2,3-trimethyl-3-cyclopenten-1-yl)pent-4-en-2-ol (Ebanol), Phenethyl isobutyrate, Florhydral, phenyl ethyl alcohol, bourgeonal, gamma-Undecalactone (racemic), Dihydromyrcenol, Ethyl 2-methyl-1,3-dioxolane-2-acetate (Fructone), Bigarade oxide, Allyl cyclohexyl propionate, Tetrahydrolinalool (Tetrahydro Linalool), Trimofix O, Citronellol, Neofolione, Hivernal mixture, Linalyl acetate, Citronellyloxyacetaldehyde, Delta-Muscenone, Romanolide, beta-Pinene, Karanal, Vertenex, o-tert-Butylcyclohexyl acetate (verdox), Nectaryl, gamma-Decalactone, Isoeugenol, Heliotropin, Oxalone (Calone 1951), Cinnamic aldehyde, Dihydro-beta-ionone, Ethyl acetate, cyclemax, Eugenol, d-Limonene, Vivaldie, Cyclogalbanate, trans-Anethole, anethole, cis-3-Hexenyl butyrate, Flor acetate, Violiff, Aurantiol, Damascenone, trans-Pinoacetaldehyde, DODECANAL, Eucalyptol, Rose oxide, Undecanal (Undecyl Aldehyde), Allyl caproate, Romascone, Allyl heptanoate, a-Irone, Hexyl acetate, Liffarome, Vertoliff, anisic aldehyde, gamma methyl ionone, NONANAL, Frutene, allyl amyl glycolate, Methyl 2-octynoate, beta-Ionone, Ethyl Oenanthate, Maltol, alpha-Damascone, Methyl-2-nonynoate, gamma-Nonalactone, Dimetol, Methyl Pamplemousse, methyl ionone (Xandralia), 2-Nonen-1-al, Oxane, (E)-2,(Z)-6-Nonadienal, Trans-2-Hexenal, ethyl butyrate, Prenyl acetate, Ethyl-2-methyl butyrate, Melonal, Isoamyl acetate, 2,6-Nonadien-1-ol, (2E,6Z)-(Nonadienol), 10% Labienone Oxim (labienoxime) in DPG, Ethyl Caproate, Phenylacetaldehyde, isobutyl quinoline, manzanate, 2-Methylundecanal, Methyl anthranilate, cis-3, cis-6-nonadienol, Ethyl vanillin, BENZALDEHYDE, Neobutenone, triplal or ligustral, 10-Undecenal, Citronellal, N-DECANAL, Vanillin, L-Carvone, Isocyclocitral, OCTANAL, Methyl benzoate, phenyl ethyl acetate, Citral, Indole, and mixtures thereof. Stemone, Cashmeran, GERANIOL, Citronellyl nitrile, Linalool, Ethyl linalool, Benzyl acetate, Undecavertol, Methyl Phenyl Carbinyl Acetate, 6-Nonen-1-ol, (6Z)-, Benzyl propionate, Iso-E Super, 2,6-Nonadien-1-ol, (2E,6Z)-(10% Nonadienol in DPG), cis-3-Hexen-1-ol (beta gamma hexenol), Isobornyl acetate, Ambrox DL, ozone propanal (Floralozone), 3-methyl-5-(2,2,3-trimethyl-3-cyclopenten-1-yl)pent-4-en-2-ol (Ebanol), Phenethyl isobutyrate, Florhydral, phenyl ethyl alcohol, bourgeonal, gamma-Undecalactone (racemic), Dihydromyrcenol, Ethyl 2-methyl-1,3-dioxolane-2-acetate (Fructone), Bigarade oxide, Allyl cyclohexyl propionate, Tetrahydrolinalool (Tetrahydro Linalool), Trimofix O, Citronellol, Neofolione, Hivernal mixture, Linalyl acetate, Citronellyloxyacetaldehyde, Delta-Muscenone, Romanolide, beta-Pinene, Karanal, Vertenex, o-tert-Butylcyclohexyl acetate (verdox), Nectaryl, gamma-Decalactone, Isoeugenol, Heliotropin, Oxalone (Calone 1951), Cinnamic aldehyde, Dihydro-beta-ionone, Ethyl acetate, cyclemax, Eugenol, d-Limonene, Vivaldie, Cyclogalbanate, trans-Anethole, anethole, cis-3-Hexenyl butyrate, Flor acetate, Violiff, Aurantiol, Damascenone, trans-Pinoacetaldehyde, DODECANAL, Eucalyptol, Rose oxide, Undecanal (Undecyl Aldehyde), Allyl caproate, Romascone, Allyl heptanoate, a-Irone, Hexyl acetate, Liffarome, Vertoliff, anisic aldehyde, gamma methyl ionone, NONANAL, Frutene, allyl amyl glycolate, Methyl 2-octynoate, beta-Ionone, Ethyl Oenanthate, Maltol, alpha-Damascone, Methyl-2-nonynoate, gamma-Nonalactone, Dimetol, Methyl Pamplemousse, methyl ionone (Xandralia), 2-Nonen-1-al, Oxane, (E)-2,(Z)-6-Nonadienal, Trans-2-Hexenal, ethyl butyrate, Prenyl acetate, Ethyl-2-methyl butyrate, Melonal, Isoamyl acetate, 2,6-Nonadien-1-ol, (2E,6Z)-(Nonadienol), 10% Labienone Oxim (labienoxime) in DPG, Ethyl Caproate, Phenylacetaldehyde, isobutyl quinoline, manzanate, 2-Methylundecanal, Methyl anthranilate, cis-3, cis-6-nonadienol, Ethyl vanillin, BENZALDEHYDE, Neobutenone, triplal or ligustral, 10-Undecenal, Citronellal, N-DECANAL, Vanillin, L-Carvone, Isocyclocitral, OCTANAL, Methyl benzoate, phenyl ethyl acetate, Citral, Indole, and mixtures thereof.

Additional suitable perfume raw materials include the following: Isoeugenol, Heliotropin, Oxalone (Calone 1951), Cinnamic aldehyde, Dihydro-beta-ionone, Ethyl acetate, cyclemax, Eugenol, d-Limonene, Vivaldie, Cyclogalbanate, trans-Anethole, anethole, cis-3-Hexenyl butyrate, Flor acetate, Violiff, Aurantiol, Damascenone, trans-Pinoacetaldehyde, DODECANAL, Eucalyptol, Rose oxide, Undecanal (Undecyl Aldehyde), Allyl caproate, Romascone, Allyl heptanoate, a-Irone, Hexyl acetate, Liffarome, Vertoliff, anisic aldehyde, gamma methyl ionone, NONANAL, Frutene, allyl amyl glycolate, Methyl 2-octynoate, beta-Ionone, Ethyl Oenanthate, Maltol, alpha-Damascone, Methyl-2-nonynoate, gamma-Nonalactone, Dimetol, Methyl Pamplemousse, methyl ionone (Xandralia), Violiff, Aurantiol, Damascenone, trans-Pinoacetaldehyde, DODECANAL, Eucalyptol, Rose oxide, Undecanal (Undecyl Aldehyde), Allyl caproate, Romascone, Allyl heptanoate, a-Irone, Hexyl acetate, Liffarome, Vertoliff, anisic aldehyde, gamma methyl ionone, NONANAL, Frutene, allyl amyl glycolate, Methyl 2-octynoate, beta-Ionone, Ethyl Oenanthate, Maltol, alpha-Damascone, Methyl-2-nonynoate, gamma-Nonalactone, Dimetol, Methyl Pamplemousse, methyl ionone (Xandralia), 2-Nonen-1-al, Oxane, (E)-2,(Z)-6-Nonadienal, Trans-2-Hexenal, ethyl butyrate, Prenyl acetate, Ethyl-2-methylbutyrate, Melonal, Isoamyl acetate, 2,6-Nonadien-1-ol, (2E,6Z)-(Nonadienol), 10% Labienone Oxim (labienoxime) in DPG, Ethyl Caproate, Phenylacetaldehyde, isobutyl quinoline, manzanate, 2-Methylundecanal, Methyl anthranilate, cis-3, cis-6-nonadienol, Ethyl vanillin, BENZALDEHYDE, Neobutenone, triplal or ligustral, 10-Undecenal, Citronellal, N-DECANAL, Vanillin, L-Carvone, Isocyclocitral, OCTANAL, Methyl benzoate, phenyl ethyl acetate, Citral, Indole, and mixtures thereof.

Further suitable perfume raw materials include the following: Violiff, Aurantiol, Damascenone, trans-Pinoacetaldehyde, DODECANAL, Eucalyptol, Rose oxide, Undecanal (Undecyl Aldehyde), Allyl caproate, Romascone, Allyl heptanoate, a-Irone, Hexyl acetate, Liffarome, Vertoliff, anisic aldehyde, gamma methyl ionone, NONANAL, Frutene, allyl amyl glycolate, Methyl 2-octynoate, beta-Ionone, Ethyl Oenanthate, Maltol, alpha-Damascone, Methyl-2-nonynoate, gamma-Nonalactone, Dimetol, Methyl Pamplemousse, methyl ionone (Xandralia), 2-Nonen-1-al, Oxane, (E)-2,(Z)-6-Nonadienal, Trans-2-Hexenal, ethyl butyrate, Prenyl acetate, Ethyl-2-methylbutyrate, Melonal, Isoamyl acetate, 2,6-Nonadien-1-ol, (2E,6Z)-(Nonadienol), 10% Labienone Oxim (labienoxime) in DPG, Ethyl Caproate, Phenylacetaldehyde, isobutyl quinoline, manzanate, 2-Methylundecanal, Methyl anthranilate, cis-3, cis-6-nonadienol, Ethyl vanillin, BENZALDEHYDE, Neobutenone, triplal or ligustral, 10-Undecenal, Citronellal, N-DECANAL, Vanillin, L-Carvone, Isocyclocitral, OCTANAL, Methyl benzoate, phenyl ethyl acetate, Citral, Indole, and mixtures thereof.

Additionally, suitable perfume raw materials include the following: 2-Nonen-1-al, Oxane, (E)-2,(Z)-6-Nonadienal, Trans-2-Hexenal, ethyl butyrate, Prenyl acetate, Ethyl-2-methylbutyrate, Melonal, Isoamyl acetate, 2,6-Nonadien-1-ol, (2E,6Z)-(Nonadienol), 10% Labienone Oxim (labienoxime) in DPG, Ethyl Caproate, Phenylacetaldehyde, isobutyl quinoline, manzanate, 2-Methylundecanal, Methyl anthranilate, cis-3, cis-6-nonadienol, Ethyl vanillin, BENZALDEHYDE, Neobutenone, triplal or ligustral, 10-Undecenal, Citronellal, N-DECANAL, Vanillin, L-Carvone, Isocyclocitral, OCTANAL, Methyl benzoate, phenyl ethyl acetate, Citral, Indole, and mixtures thereof.

According to various embodiments, the disclosed fragrance compositions may optionally include one or more additional ingredients or excipients conventionally used in conjunction with fragrances in perfume compositions, for example carrier materials, and other auxiliary agents commonly used in the art, e.g., solvents, preservatives, antifungals, emulsifiers, stabilizers and the like. In various embodiments, the fragrance composition may include one or more solvents such as, e.g., alcohol, hydroalcohol, water, propylene glycol, dipropylene glycol (DPG), isopropyl myristate (IPM), and triethyl citrate (TEC), or combinations thereof.

According to some embodiments, a method of preparing the disclosed fragrance compositions includes combining one or more fragrance compounds with a glycoside. Advantageously, the steviol glycosides can be added to fragrance compounds in ambient conditions. In the examples, the compositions of the present disclosure were added at room temperature and atmospheric pressure.

According to some embodiments, a glycoside can be added to a product or article including one or more fragrance compounds.

According to some embodiments, the fragrance compositions disclosed herein may be used in a broad range of non-food and/or non-beverage articles and applications. For example, the fragrance compositions may be used in fragrance products and applications comprising an odorant, for example, in any field of fine and functional perfumery, such as perfumes, household products, laundry products, body care products and cosmetics. Specific exemplary and non-limiting examples include fine fragrances (e.g. eau de perfume and eau de toilette); household products (e.g. dishwashing detergents, surface cleaners, air fresheners, automotive care products, hard surface cleaning and/or treatment agents (including floor and toilet bowl cleaners), and other cleaning products for consumer or institutional use. cleaning detergents, in particulate or powder form; multifunctional detergents in the form of liquids, gels or pastes; liquid fine fabric detergents; hand dishwashing detergents; machine dishwashing detergents, including various tablet, granular, liquid and rinse aid types for home and institutional use; liquid cleaning and disinfecting agents including antibacterial hand-wash types, cleaning bars, car or carpet detergents, bathroom cleaners including toilet bowl cleaners; and metal cleaners, fabric conditioning products including softeners and/or fresheners, which may be in the form of liquid, solid and/or desiccant tablets; and cleaning adjuvants such as bleach additives and "stain-stick" or pretreatment type, substrate-laden products such as dryer-incorporated sheets, dry and wet wipes and pads, nonwoven substrates and sponges; as well as sprays and mists; products and/or processes relating to toilet tissue, facial tissue, handkerchiefs and/or paper towels; tampons, feminine sanitary napkins; laundry products (e.g. softener, bleach, detergent, stain/odor treatment); body care products for human or pet use (e.g. after-shave lotion, soap, shampoo, hair conditioner, shower gel, shower and bath salt, hair products, body lotion, sunscreen, hygiene products); and cosmetics (e.g. deodorants, antiperspirants, vanishing creams, makeup products).

According to the various embodiments, the article comprises an effective amount of the fragrance composition to provide a desired fragrance.

An embodiment of the present disclosure provides for a perfume comprising water; a solvent, a glycoside, and a fragrance compound. The fragrance compound can be an oil, wherein the oil is in a concentration of about 1 to 20% by weight. The oil can be a perfume oil or essential oil. In some embodiments, the solvent can be an alcohol. In some embodiments, the alcohol can be ethanol. The glycoside can be from about 0.01 to 5.0% of the perfume by weight, about 0.1 to 1.0% of the perfume by weight, or about 0.1 to 0.5% of the perfume by weight.

An embodiment of the present disclosure provides for a perfume consisting of water; one or more solvents, one or more glycosides, and one or more fragrance compounds. The fragrance compound can be an oil, wherein the oil is in a concentration of about 1 to 20% by weight. The oil can be a perfume oil or essential oil. In some embodiments, the solvent can be an alcohol. In some embodiments, the alcohol can be ethanol. The glycoside can be from about 0.01 to 5.0% of the perfume by weight, about 0.1 to 1.0% of the perfume by weight, or about 0.1 to 0.5% of the perfume by weight.

An embodiment of the present disclosure provides for a perfume consisting essentially of water; one or more solvents, one or more glycosides, and one or more fragrance compounds. The fragrance compound can be an oil, wherein the oil is in a concentration of about 1 to 20% by weight. The oil can be a perfume oil or essential oil. In some embodiments, the solvent can be an alcohol. In some embodiments, the alcohol can be ethanol. The glycoside can be from about 0.01 to 5.0% of the perfume by weight, about 0.1 to 1.0% of the perfume by weight, or about 0.1 to 0.5% of the perfume by weight. The phrase "consisting essentially of" as used in this regard refers to the perfume including other components do not materially affect the basic and novel characteristic(s) of the perfume such as those that might be found in trace amounts or other components that do not alter the fixative characteristics of the perfume but might be found in a perfume otherwise. The phrase "consisting essentially of" as applied to perfumes is an open-ended term, allowing for the presence of one or more components that might be found in a perfume than those recited so long as basic or novel characteristics of that which is recited is not changed by the presence of one or more of the components other than those recited, but excludes prior art embodiments, Embodiments of the present disclosure provide for non-comestible products comprising at least one fragrance compound, a glycoside, and an anionic surfactant.

Embodiments of the present disclosure provide for non-comestible products comprising sodium hypochlorite, at least one fragrance compound, and a glycoside.

Embodiments of the present disclosure provide for non-comestible products comprising at least one fragrance compound, a glycoside, an enzyme protein, and a surfactant.

Embodiments of the present disclosure provide for non-comestible detergents comprising at least one fragrance compound, a glycoside, an enzyme protein, and a detergent surfactant. In some embodiments, the non-comestible detergent can include a whitening agent.

Embodiments of the present disclosure provide for non-comestible products comprising sodium carbonate, citric acid, at least one fragrance compound, and a glycoside.

Embodiments of the present disclosure provide for non-comestible products comprising ammonia, at least one fragrance compound, and a glycoside.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Unless otherwise specified all percentages noted in the examples are weight/weight. In the examples provided below, panel studies were conducted to evaluate the efficacy of steviol glycosides as a fragrance fixative, and to determine whether the addition of the glycosides negatively affected participants' preferences for fragrances. Fragrance strength and duration is not easily measured quantitatively, so rather can be characterized based on human evaluations. To qualitatively evaluate fragrance, panel studies were conducted as follows. In each of the panels, there were ten participants. For non-skin applications, a blotting paper (perfume test strip, or Mouillette) was dipped one third of its length into the fragrance composition and left in the open air. Panel participants were asked to evaluate the fragrance over a 48-hour period, with observations recorded at 2 hours, 4 hours, 6 hours, 12 hours, 24 hours, and 48 hours. For skin applications, a single spray was applied from a distance of 6 inches to the participant's wrist and allowed to dry for 20 seconds. The panel participants were asked to evaluate the fragrance, with observations recorded every 2 hours for 8 hours. Participants indicated preference by indicating a preference for one scent over the other and ranked the strength of the scents by stronger, equal, or weaker.

Example 1—Perfume

In this example, an exemplary fragrance composition comprising a fragrance compound and a steviol-based glycoside was prepared and compared to a control composition comprising the same fragrance compound, but no glycoside. The recipes for comparative composition 1-A and exemplary fragrance composition 1-B are provided in Table 1.

TABLE 1

|  | 1-A | 1-B |
|---|---|---|
| Aldehydic-Floral Perfume Oil | 12.0% | 12.0% |
| Steviol Glycosides (Rebaudioside A 80%) | 0.0% | 0.5% |
| Alcohol | 88.0% | 87.5% |
| Total | 100.0% | 100.0% |

In panel studies, in periods ranging from one to 48 hours, 90% of the panelists observed longer lasting properties (e.g. about 36 hours) on skin in the exemplary formulation with 0.5% Rebaudioside A 80% (1-B) compared to the formulation without steviol glycosides (1-A). On tests on perfume blotters that lasted 48 hours, 90% of the panelists made the same observation.

Example 2—After Bath Splash

In this example, an after-bath splash product was prepared having an exemplary fragrance composition comprising a fragrance compound and a steviol-based glycoside and compared to an after-bath splash product having a control composition comprising the same fragrance compound, but no glycoside. The recipes for comparative bath-splash composition 2-A and exemplary bath-splash composition 2-B are provided in Table 2.

TABLE 2

|  | 2-A | 2-B |
|---|---|---|
| Citrus-Lavender Fougere Perfume Oil | 12.0% | 12% |
| Steviol Glycosides (Rebaudioside A 97%) | 0.0% | 0.1% |
| Alcohol | 66.2% | 66.1% |
| Water | 21.8% | 21.8% |
| Total | 100% | 100% |

In panel studies, 90% of the panelists observed longer lasting properties on skin in the exemplary formulation with 0.1% Rebaudioside A 97% (2-B) compared to the comparative formulation without the steviol glycosides (2-A). The panelists observed that in the exemplary formulation (2-B), the fragrances lasted 48 hours longer. On tests on perfume blotters, 100% of the panelists made the same observation.

Example 3—Eau De Toilet

In this example, an exemplary fragrance composition comprising a fragrance compound and a steviol-based glycoside was prepared and compared to a control composition comprising the same fragrance compound, but no glycoside. The recipes for comparative composition 3-A and exemplary fragrance composition 3-B are provided in Table 3.

TABLE 3

|  | 3-A | 3-B |
|---|---|---|
| Herbal Woody Perfume Oil | 8.0% | 8.0% |
| Steviol Glycosides (Rebaudioside A 50%) | 0.0% | 0.1% |
| Alcohol | 86.0% | 85.9% |
| Water | 6.0% | 6.0% |
| Total | 100% | 100% |

In panel studies, 90% of the panelists preferred the fragrance of the exemplary formulation with Rebaudioside A 50% (3-B) on skin to that of the comparative composition 3-A. On perfume blotters, 100% of the panelists preferred the fragrance of the exemplary formulation 3-B.

Example 4—Cologne

In this example, an exemplary fragrance composition comprising a fragrance compound and a steviol-based glycoside was prepared and compared to a control composition comprising the same fragrance compound, but no glycoside. The recipes for comparative composition 4-A and exemplary fragrance composition 4-B are provided in Table 4.

TABLE 4

|  | 4-A | 4-B |
| --- | --- | --- |
| Citrus Floral Perfume Oil | 5.0% | 5.0% |
| Steviol Glycosides (GSG 80%) | 0.0% | 0.1% |
| Alcohol | 75.0% | 74.9% |
| Water | 20.0% | 20.0% |
| Total | 100% | 100% |

In panel studies, 90% of the panelists preferred the fragrance of the cologne including the Steviol Glycosides (GSG 80%) (4-B) on skin as compared to the comparative cologne that excluded the glycoside. On perfume blotters, 90% of the panelists preferred the fragrance of the exemplary cologne product 4-B.

Example 5—After Shave Lotion

In this example, a shave lotion was prepared having an exemplary fragrance composition comprising a fragrance compound and a steviol-based glycoside and compared to a shave lotion having a control composition comprising the same fragrance compound, but no glycoside. The recipes for comparative shave lotion composition 5-A and exemplary shave lotion fragrance composition 5-B are provided in Table 5.

TABLE 5

|  | 5-A | 5-B |
| --- | --- | --- |
| Spanish Leather Perfume Oil | 0.6% | 0.6% |
| Steviol Glycosides (GSG 90%) | 0.0% | 0.5% |
| Alcohol | 63.0% | 62.5% |
| Water | 36.4% | 36.4% |
| Total | 100% | 100% |

In panel studies over periods ranging from one to twenty-four hours, 90% of the panelists determined longer lasting properties on skin for the product with Steviol Glycosides (GSG 90%) (5-B) compared to the product without this steviol glycosides (5-A). On perfume blotters, 80% of the panelists preferred the lasting quality of the (5-B) product.

Example 6—Hand Cream

In this example, a hand cream was prepared having an exemplary fragrance composition comprising a fragrance compound and a steviol-based glycoside and compared to a hand cream having a control composition comprising the same fragrance compound, but no glycoside. The recipes for comparative hand cream composition 6-A and exemplary hand cream composition 6-B are provided in Table 6.

TABLE 6

|  | 6-A | 6-B |
| --- | --- | --- |
| Floral Perfume Oil | 0.6% | 0.6% |
| Steviol Glycosides (GSG 90%) | 0.0% | 0.2% |
| Albagel | 1.5% | 1.5% |
| Stearic Acid | 2.0% | 2.0% |
| Mineral Oil | 6% | 6% |
| Cetyl Alcohol | 2.0% | 2.0% |
| Acetylated Lanolin | 2% | 2% |
| Methyl Glucoside Sesquistearate | 0.8% | 0.8% |
| Glycerin | 5% | 5% |
| Water | 86.1% | 85.9% |
| Total | 100% | 100% |

Over a period of one to four hours, the hand cream with Steviol Glycosides (GSG 90%)(6-B) was judged by 80% of the panelists to exhibit a fragrance having greater intensity and longer lasting power than the fragrance of the comparative hand cream without the steviol glycoside (6-A).

Example 7—Soap Bars

In this example, a soap bar was prepared having an exemplary fragrance composition comprising a fragrance compound and a steviol-based glycoside and compared to a soap bar having a control composition comprising the same fragrance compound, but no glycoside. The recipes for control soap bar composition 7-A and exemplary soap bar composition 7-B are provided in Table 7.

TABLE 7

|  | 1-A | 1-B |
| --- | --- | --- |
| Lilac Perfume Oil | 1.5% | 1.5% |
| Steviol Glycosides (GSG 90%) | 0.0% | 0.3% |
| Soap Stock | 98.5% | 98.2% |
| Total | 100% | 100.0% |

In wash use tests, 90% of the panelists judged the intensity of fragrance in soap bars containing Steviol Glycosides (GSG 90%) (7-B) to be greater than that in bars without the Steviol Glycosides (GSG 90%). In the wash use test, half of the panelists were instructed to wash their hands using their normal handwashing procedure with soap bars containing steviol glycosides while the other half of the panelists used the soap bars without the steviol glycosides.

Example 8—Reduction of Perfume Oil Concentration in Perfume

In this example, an exemplary fragrance composition comprising a fragrance compound and a steviol-based glycoside was prepared and compared to a control composition comprising the same fragrance compound, but no glycoside. The recipes for comparative composition 8-A and exemplary fragrance composition 8-B are provided in Table 8.

TABLE 8

|  | 8-A | 8-B |
| --- | --- | --- |
| Aldehydic-Floral Perfume Oil | 12.0% | 10.0% |
| Steviol Glycosides (Reb A 80%) | 0.0% | 0.5% |
| Alcohol | 88.0% | 89.5% |
| Total | 100% | 100.0% |

In panel tests on skin and perfume blotters, 40% of the panelists judged exemplary Formula 8-B to have a stronger fragrance than comparative Formula 8-A. The remaining 60% judged 8-A and 8-B to have equivalent fragrance. This indicates that by using the glycoside in the fragrance composition, it may be possible to reduce the amount of fragrance compound without diminishing the perceived fragrance of the fragrance composition. Use of such reduced concentration of perfume oils without adverse effect on perception of odor will provide significant savings in material costs.

Example 9—Reduction of Perfume Oil Concentration in Colognes

In this example, an exemplary fragrance composition comprising a fragrance compound and a steviol-based glycoside was prepared and compared to a control composition comprising the same fragrance compound, but no glycoside. The recipes for comparative composition 9-A and exemplary fragrance composition 9-B are provided in Table 9.

TABLE 9

|  | 9-A | 9-B |
| --- | --- | --- |
| Citrus-Floral Perfume Oil | 5.0% | 4.0% |
| Steviol Glycosides (Reb A 80%) | 0.0% | 0.1% |
| Alcohol | 95.0% | 95.9% |
| Total | 100% | 100.0% |

In panel tests, 40% of the panelists judged Formula 9-B with Steviol Glycosides (Reb A 80%) to have a stronger fragrance than Formula 9-A without the Steviol Glycosides (Reb A 80%); 30% found no difference between the two fragrances; and 30% judged 9-A to have a stronger fragrance. Thus 70% of the panelists accepted the exemplary fragrance composition having reduced perfume oil concentration as equal to or better than the comparative composition. This indicates that by using the glycoside, it may be possible to reduce the amount of fragrance compound without diminishing the perceived fragrance, but with possible attendant major cost savings. Tests were run on skin and blotters.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, "about 0" can refer to 0, 0.001, 0.01, or 0.1. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

What is claimed is:

1. A fragrance composition for a non-comestible product comprising:
   at least one fragrance compound; and
   a glycoside selected from a Steviol glycoside, a glucosylated Steviol glycoside, a derivative of a Steviol glycoside, a derivative of a glucosylated Steviol glycoside, or combinations thereof;
   wherein the glycoside is a fragrance fixative such that by inclusion of the glycoside:
      a perceived duration of fragrance is increased by addition of the glycoside, or
      a perceived strength of the fragrance compound is undiminished when reduced by about 1% to 2%.

2. The fragrance composition of claim 1, further comprising a solvent, wherein the solvent is selected from alcohol, hydroalcohol, water, propylene glycol, or a combination thereof.

3. The fragrance composition of claim 1, wherein the glycoside comprises from about 0.001 to 0.5 weight % based on a total weight of the fragrance composition.

4. The fragrance composition of claim 1 wherein the glycoside is a Steviol glycoside selected from Rebaudioside A, Rebaudioside B, Rebaudioside C, Rebaudioside D, Rebaudioside E, Rebaudioside F, Rebaudioside M, Rebaudioside N, Rebaudioside O.

5. The fragrance composition of claim 1, wherein the Steviol glycoside is enzymatically treated *stevia* extract.

6. The fragrance composition of claim 1, wherein the glucosylated Steviol glycoside has a low degree of glycosylation, where the number of glucose molecules attached to the steviol glycoside is from one to five.

7. The fragrance composition of claim 1, wherein the glucosylated Steviol glycoside has a high degree of glycosylation where the number of glucose molecules attached to the steviol glycoside is from six to ten.

8. A non-comestible product including a fragrance composition, the fragrance composition comprising at least one fragrance compound; and
   a glycoside selected from a Steviol glycoside, a glucosylated Steviol glycoside, a derivative of a Steviol glycoside, a derivative of a glucosylated Steviol glycoside, or combinations thereof;
      wherein the glycoside is a fragrance fixative such that by inclusion of the glycoside:
         a perceived duration of fragrance is increased by addition of the glycoside, or
         a perceived strength of the fragrance compound is undiminished when reduced by about 1% to 2%.

9. The product of claim 8, wherein the product is selected from a perfume, a toilet water, a lotion, a soap, a cosmetic, or a body care product.

10. The product of claim 8, wherein the product is selected from a dishwashing detergent, a surface cleaner, an air freshener, a softener, a bleach, or a laundry detergent.

11. The product of claim 8, further comprising a solvent, wherein the solvent is selected from alcohol, hydroalcohol, water, propylene glycol, or a combination thereof.

12. The product of claim 8, wherein the glycoside comprises from about 0.001 to 0.5 weight % based on a total weight of the fragrance composition.

13. The product of claim 8, wherein the glycoside is a Steviol glycoside selected from Rebaudioside A, Rebaudioside B, Rebaudioside C, Rebaudioside D, Rebaudioside E, Rebaudioside F, Rebaudioside M, Rebaudioside N, Rebaudioside O.

14. The product of claim 8, wherein the Steviol glycoside is enzymatically treated *stevia* extract.

15. The product of claim 8, wherein the glucosylated Steviol glycoside has a low degree of glycosylation, where the number of glucose molecules attached to the steviol glycoside is from one to five.

16. The product of claim 8, wherein the glucosylated Steviol glycoside has a high degree of glycosylation where the number of glucose molecules attached to the steviol glycoside is from six to ten.

17. A non-comestible product comprising a perfume, the perfume comprising water, ethanol, a glycoside, and a fragrance compound;
wherein the glycoside is a fragrance fixative.

18. The non-comestible product of claim 17, wherein the glycoside is selected from a Steviol glycoside, a glucosylated Steviol glycoside, a derivative of a Steviol glycoside, a derivative of a glucosylated Steviol glycoside, or combinations thereof.

19. The non-comestible product of claim 17, further comprising alcohol, hydroalcohol, water, propylene glycol, or a combination thereof.

20. The non-comestible product of claim 17, wherein the glycoside comprises from about 0.001 to 0.5 weight % based on a total weight of the fragrance composition.

* * * * *